(12) United States Patent
Kampen et al.

(10) Patent No.: US 9,393,104 B2
(45) Date of Patent: *Jul. 19, 2016

(54) TENDON REPAIR IMPLANT AND METHOD OF ARTHROSCOPIC IMPLANTATION

(71) Applicant: Rotation Medical, Inc., Plymouth, MN (US)

(72) Inventors: Craig Van Kampen, Oakdale, MN (US); Nathaniel Zenz-Olson, Blaine, MN (US); Thomas A. Westling, Orono, MN (US); Charles L. Euteneuer, St. Michael, MN (US)

(73) Assignee: Rotation Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,989

(22) Filed: Sep. 2, 2014

(65) Prior Publication Data

US 2014/0371853 A1 Dec. 18, 2014

Related U.S. Application Data

(63) Continuation of application No. 13/889,701, filed on May 8, 2013, which is a continuation of application No. 13/046,624, filed on Mar. 11, 2011, now Pat. No. 9,198,750.

(60) Provisional application No. 61/313,113, filed on Mar. 11, 2010.

(51) Int. Cl.
*A61F 2/08* (2006.01)
*A61F 2/00* (2006.01)
(Continued)

(52) U.S. Cl.
CPC ............... *A61F 2/08* (2013.01); *A61F 2/0805* (2013.01); *A61F 2/0077* (2013.01);
(Continued)

(58) Field of Classification Search
CPC . A61F 2/08; A61F 2002/0894; A61F 2/0063; A61F 2002/0068; A61F 2002/0081; A61F 2002/0086; A61F 2210/0004; A61F 2210/0057

See application file for complete search history.

(56) References Cited

U.S. PATENT DOCUMENTS

| 511,238 A | 12/1893 | Hieatzman |
| 765,793 A | 7/1904 | Ruckel |

(Continued)

FOREIGN PATENT DOCUMENTS

| CA | 2390508 A1 | 5/2001 |
| EP | 0142225 A1 | 5/1985 |

(Continued)

OTHER PUBLICATIONS

Euteneuer et al.; U.S. Appl. No. 13/717,474 entitled "Apparatus and Method for Forming Pilot Holes in Bone and Delivering Fasteners Therein for Retaining an Implant," filed Dec. 17, 2012.

(Continued)

*Primary Examiner* — Andrew Iwamaye
(74) *Attorney, Agent, or Firm* — Seager, Tufte & Wickhem LLP

(57) ABSTRACT

A tendon repair implant for treatment of a partial thickness tear in the supraspinatus tendon of the shoulder is provided. The implant may incorporate features of rapid deployment and fixation by arthroscopic means that compliment current procedures; tensile properties that result in desired sharing of anatomical load between the implant and native tendon during rehabilitation; selected porosity and longitudinal pathways for tissue in-growth; sufficient cyclic straining of the implant in the longitudinal direction to promote remodeling of new tissue to tendon-like tissue; and, may include a bioresorbable construction to provide transfer of additional load to new tendon-like tissue and native tendon over time.

32 Claims, 9 Drawing Sheets

(51) Int. Cl.
*A61L 27/36* (2006.01)
*A61L 27/24* (2006.01)
*A61L 27/56* (2006.01)
*A61L 27/58* (2006.01)
*A61L 27/54* (2006.01)

(52) U.S. Cl.
CPC  *A61F 2002/0068* (2013.01); *A61F 2002/0894* (2013.01); *A61F 2210/0004* (2013.01); *A61F 2210/0057* (2013.01); *A61F 2210/0076* (2013.01); *A61F 2230/0019* (2013.01); *A61F 2250/0067* (2013.01); *A61L 27/24* (2013.01); *A61L 27/3662* (2013.01); *A61L 27/54* (2013.01); *A61L 27/56* (2013.01); *A61L 27/58* (2013.01); *A61L 2430/10* (2013.01); *A61L 2430/30* (2013.01); *A61L 2430/34* (2013.01)

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Charles |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,570,497 A | 10/1951 | Senderowitz |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens |
| 3,643,851 A | 2/1972 | Green |
| 3,687,138 A | 8/1972 | Jarvik |
| 3,716,058 A | 2/1973 | Tanner |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy et al. |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Goble et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst et al. |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach et al. |
| 5,122,155 A | 6/1992 | Eberbach et al. |
| 5,123,913 A | 6/1992 | Wilk et al. |
| RE34,012 E | 7/1992 | Azuma et al. |
| 5,141,515 A | 8/1992 | Eberbach et al. |
| 5,141,520 A | 8/1992 | Goble |
| 5,156,609 A | 10/1992 | Nakao et al. |
| 5,156,616 A | 10/1992 | Meadows et al. |
| 5,167,665 A | 12/1992 | McKinney et al. |
| 5,171,259 A | 12/1992 | Inoue |
| 5,171,273 A * | 12/1992 | Silver et al. ............... 623/13.11 |
| 5,174,295 A | 12/1992 | Christian et al. |
| 5,174,487 A | 12/1992 | Rothfuss et al. |
| 5,176,682 A | 1/1993 | Chow et al. |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook et al. |
| 5,350,400 A | 9/1994 | Esposito et al. |
| 5,352,229 A | 10/1994 | Goble |
| 5,354,292 A | 10/1994 | Braeuer et al. |
| 5,364,408 A | 11/1994 | Gordon et al. |
| 5,366,460 A | 11/1994 | Eberbach et al. |
| 5,370,650 A | 12/1994 | Tovey et al. |
| 5,372,604 A | 12/1994 | Trott |

(56) References Cited

U.S. PATENT DOCUMENTS

| | | |
|---|---|---|
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott et al. |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett et al. |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield et al. |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst et al. |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach et al. |
| 5,766,243 A | 6/1998 | Christensen et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn et al. |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,702,215 B2 | 3/2004 | Stamm et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 * | 9/2005 | Wolowacz et al. ......... 623/23.72 |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén et al. |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |

(56) References Cited

U.S. PATENT DOCUMENTS

| | | |
|---|---|---|
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,801,801 B2 * | 8/2014 | Datta et al. ............... 623/23.72 |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0121456 A1 | 7/2003 | Griffith et al. |
| 2003/0125748 A1 | 7/2003 | Li et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard |
| 2008/0090936 A1 | 4/2008 | Fujimura et al. |
| 2008/0125869 A1 | 5/2008 | Paz |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0063599 A1 * | 3/2010 | Brunelle et al. ............ 623/23.72 |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0256777 A1 * | 10/2010 | Datta et al. ................. 623/23.72 |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0184530 A1 | 7/2011 | Datta et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0248171 A1 | 10/2012 | Bailly et al. |
| 2012/0316608 A1 | 12/2012 | Foley |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 * | 9/2013 | Van Kampen et al. .... 623/13.18 |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |

(56) References Cited

FOREIGN PATENT DOCUMENTS

| | | |
|---|---|---|
| GB | 2154688 A | 9/1985 |
| GB | 2397240 A | 7/2004 |
| JP | 58188442 | 11/1983 |
| JP | 2005506122 | 3/2005 |
| JP | 2006515774 | 6/2006 |
| WO | 8505025 | 11/1985 |
| WO | 0176456 A2 | 10/2001 |
| WO | 0234140 A2 | 5/2002 |
| WO | 03105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |

OTHER PUBLICATIONS

Euteneuer et al.; U.S. Appl. No. 13/717,493 entitled "Fasteners and Fastener Delivery Devices for Afficing Sheet-Like Materials to Bone or Tissue," filed Dec. 17, 2012.
Euteneuer et al.; U.S. Appl. No. 13/717,515 entitled "Fasteners and Fastener Delivery Devices for Affixing Sheet-Like Materials to Bone or Tissue," filed Dec. 17, 2012.
Euteneuer et al.; U.S. Appl. No. 13/717,530 entitled "Fasteners and Fastener Delivery Devices for Afficing Sheet-Like Materials to Bone or Tissue," filed Dec. 17, 2012.
Euteneuer et al.; U.S. Appl. No. 13/722,796 entitled "Methods and Apparatus for Delivering and Positioning Sheet-Like Materials in Surgery," filed Dec. 20, 2012.
Euteneuer et al.; U.S. Appl. No. 13/722,865 entitled "Guidewire Having a Distal Fixation Member for Delivering and Positioning Sheet-Like Materials in Surgery," filed Dec. 20, 2012.
Euteneuer et al.; U.S. Appl. No. 13/722,940 entitled "Anatomical Location Markers and Methods of Use in Positioning Sheet-Like Materials During Surgery," filed Dec. 20, 2012.
Euteneuer et al.; U.S. Appl. No. 13/763,414 entitled "Implantable Tendon Protection Systems and Related Kits and Methods," filed Feb. 8, 2013.
Euteneuer, Charles L.; U.S. Appl. No. 13/397,573 entitled "Methods and Apparatus for Fixing Sheet-Like Materials to a Target Tissue," filed Feb. 15, 2012
Euteneuer et al.; U.S. Appl. No. 13/397,603 entitled "Methods and Apparatus for Delivering and Positioning Sheet-Like Materials," filed Feb. 15, 2012.

Alexander et al.; Ligament and tendon repair with an absorbable polymer-coated carbon fiber stent; Bulletin of the Hospital for Join Diseases Orthopaedic Institute; vol. 46; No. 2; pp. 155-173; 1986.
Bahler et al.; Trabecular bypass stunts decrease intaocular pressure in cultured himan anterior segments; Am. J. Opthalmology; vol. 138; No. 6; pp. 988-994; Dec. 2004.
Chamay et al.; Digital contracture deformity after implantation of silicone prosthesis: Light and electron microscopic study; The Journal of Hand Surgery; vol. 3; No. 3; pp. 266-270; May 1978.
D'Ermo et al. Our results with the operation of ab externo; Ophthalmologica; vol. 168; pp. 347-355; 1971.
France et al.; Biomechanical evaluation of rotator cuff fixation methods; The American Journal of Sports Medicine; vol. 17; No. 2; 1989.
Goodship et al.; An assessment of filamentous carbon fibre for the treatment of tendon injury in the horse; Veterinary record; vol. 106; pp. 217-221; Mar. 8, 1980.
Hunter et al.; Flexor-tendon reconstruction in severely damaged hands; The Journal of Bone and Joint Surgery (American Volume); vol. 53-A; No. 5; pp. 329-358; Jul. 1971
Johnstone et al.; Microsurgery of Schlemm's canal and the human aqueous outflow system; Am. J. Ophthalmology; vol. 76; No. 6; pp. 906-917; Dec. 1973.
Kowalsky et al.; Evaluation of suture abrasion against rotator cuff tenon and proximal humerus bone; Anthroscopy: The Journal of Arthroscopic and Related Surgery; 2008.
Lee et al.; Aqueous-venous and intraocular pressure. Preliminary report of animal studies; Investigative Ophthalmology; vol. 5; No. 1; pp. 59-64; Feb. 1966.
Meapea et al.; the Pressures in the episcleral veins, Schlemm's canal and the trabecular meshwork in monkeys: Effects of changes in intraocular pressure; Exp. Eye Res.; vol. 49; pp. 645-663; 1989.
Nicolle et al.; A silastic tendon prosthesis as an adjunct to flexor tendon grafting: And experimental an clinical evaluation; British Journal of Plastic Surgery; vol. 22; Issues 3-4; pp. 224-236; 1969.
Rubin et al.; the use of acellular biologic tissue patches in foot and ankle surgery; Clinics in Podiatric Medicine and Surgery; vol. 22; pp. 533-552; 2005.
Schultz et al.; Canaloplasty procedure shows promise for open-angle glaucoma in European study; Ocular Surgery News; pp. 34-35; Mar. 1, 2007
Spiegel et al.; Schlemm's canal implant: A new method to lower intraocular pressure in patients of POAG; Ophthalmic Surgery and Lasers; vol. 30; No. 6; pp. 492-494; Jun. 1999.
Valdez et al.; Repair of digital flexor tendon lacerations in the horse, using carbon fiber implants; JAYMA; vol. 177; No. 5; pp. 427-435; Sep. 1, 1980.
Zobitz et al.; Determination of the compressive materials properties of the supraspinatus tendon; J. Biomech. Eng.; vol. 123(1): Feb. 2001 (Abstract).
William B. Stetson, MD, Richard K.N. Ryu, MD, and Edward S. Bittar, MD, PhD, Arthroscopic Treatment of Partial Rotator Cuff Tears, 2004, pp. 135-148, Sports Medicine, University of Southern California, Glendale, CA 91103.
Ryan P. Finnan, MD, Lynn A. Crosby, MD, "Partial-thickness rotator cuff tears", J Shoulder Elbow Surg (2010) 19, pp. 609-616.

* cited by examiner

TENDON REPAIR IMPLANT AND METHOD OF ARTHROSCOPIC IMPLANTATION

CROSS REFERENCE TO RELATED APPLICATIONS

This application is a continuation of U.S. application Ser. No. 13/889,701 filed on May 8, 2013, which is a continuation of U.S. application Ser. No. 13/046,624 filed on Mar. 11, 2011, which claims benefit to U.S. Provisional Patent Application No. 61/313,113, filed on Mar. 11, 2010. The disclosures of each of which are herein incorporated by reference in their entirety.

INCORPORATION BY REFERENCE

This present application is related to: U.S. patent application Ser. No. 12/684,774, filed Jan. 8, 2010; U.S. patent application Ser. No. 12/729,029, filed Mar. 22, 2010; U.S. patent application Ser. No. 12/794,540, filed Jun. 4, 2010; U.S. patent application Ser. No. 12/794,551, filed Jun. 4, 2010; U.S. patent application Ser. No. 12/794,673, filed Jun. 4, 2010; U.S. patent application Ser. No. 12/794,677, filed Jun. 4, 2010; U.S. patent application Ser. No. 13/889,701; U.S. Provisional Patent Application No. 61/443,180, filed Feb. 15, 2011; U.S. Provisional Patent Application No. 61/443,169, filed Feb. 15, 2011, all of which are incorporated herein by reference.

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic implants and methods of treatment. More particularly, the present invention relates to a tendon repair implant, such as one that is engineered for arthroscopic placement over or in the area of a partial thickness tear in the supraspinatus tendon of the shoulder.

BACKGROUND OF THE INVENTION

As disclosed by Ball et al. in U.S. Patent Publication No. U.S. 2008/0188936A1 and illustrated in FIG. 1, the rotator cuff 10 is the complex of four muscles that arise from the scapula 12 and whose tendons blend in with the subjacent capsule as they attach to the tuberosities of the humerus 14. The subscapularis 16 arises from the anterior aspect of the scapula 12 and attaches over much of the lesser tuberosity. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11. Proper functioning of the rotator depends on the fundamental centering and stabilizing role of the humeral head 15 with respect to sliding action during anterior and lateral lifting and rotation movements of the arm.

The insertion of these tendons as a continuous cuff 10 around the humeral head 17 permits the cuff muscles to provide an infinite variety of moments to rotate the humerus 14 and to oppose unwanted components of the deltoid and pectoralis muscle forces. The insertion of the infraspinatus 13 overlaps that of the supraspinatus 18 to some extent. Each of the other tendons 16, 15 also interlaces its fibers to some extent with its neighbor's tendons. The tendons splay out and interdigitate to form a common continuous insertion on the humerus 14.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

The mechanics of the rotator cuff 10 are complex. The cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinatus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In treating a full thickness tear or partial thickness tear of greater than 50% after completing the tear by cutting the tendon, accepted practice also can include the placement of scaffolds and patches over the repaired tendon to shield the sutured or repaired tendon area from anatomical load during rehabilitation. For example, Wright Medical disclose that the Graft-Jacket® can be used to augment a suture repaired tendon in large and massive full-thickness tears or smaller full-thickness tears in a shoulder having severely degenerated tissue. However, it is recognized that significant shielding of the tendon from load can lead to atrophy and degeneration of the native tendon and muscle.

It is known that, for the rotator cuff, allowing the tendon to experience full anatomical load during recovery after repairing the tendon tear with sutures will result in a 20-60% failure rate. Ball et al. (U.S. Patent Appl. No. 2008/0188936 A1) disclose an implant that provides a healing modality that shields the tendon from most of the anatomical loads in the early part of the recovery period, and gradually experience increasing loads as the repair heals to full strength. Ball et al. discloses the strength of the surgical repair, expressed as percent strength of the final healed repair, begins post-surgically at the strength of the suture-to-tissue connection alone. In their illustrated example, the suture-to-tissue connection represents about 25% of the strength. The augmentation implant initially receives the 75% of the loads experienced during recovery through high initial strength. Gradually, the ratio of load sharing shifts to the suture-to-tissue connection as the repair heals and gains strength, while the implant is simultaneously absorbed by the body. Strength retention is defined to refer to the amount of strength that a material maintains over a period of time following implantation into a human or animal. For example, if the tensile strength of an absorbable mesh or fiber decreases by half over three months when implanted into an animal or human, the mesh or fiber's strength retention at 3 months would be 50%.

In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%. However, current treatment interventions do not include repair of the tendon. Rather, the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure. Again, the tendon partial tear is not repaired. Several authors have reported satisfactory early post-operative results from these procedures, but over time recurrent symptoms have been noted. In the event of recurrent symptoms, many times a patient will "live with the pain". This may result in less use of the arm and shoulder which further causes degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE INVENTION

In accordance with aspects of the disclosure, a tendon repair implant is provided that can be relatively quickly implanted during an arthroscopic procedure to treat symptoms related to a partial thickness tear, such as in the supraspinatus tendon of the shoulder. With current treatment modalities, a partial thickness tear is treated without repair of the tendon itself, but rather procedures are directed to removing bone that may be impinging upon or restricting movement of the tendon. Other current procedures may include debridement of degenerated tendon, but again nothing is done to repair the tendon.

In some embodiments, the tendon repair implant can include a sheet-like structure having desired properties and format for repairing the partial thickness tear. In particular, the sheet-like structure may be constructed to have a first compact configuration for delivery from an arthroscopic instrument and a second planar configuration defined by a longitudinal, lateral and thickness dimension with a longitudinal surface generally conformable to a bursal side surface of the supraspinatus tendon when positioned thereon. The sheet-like structure may have a tensile modulus of about 5 MPa to about 100 MPa in the range of 1% to 3% strain in the longitudinal dimension and porosity of about 30% to about 90%. Further the sheet-like structure may include longitudinal pathways defined in the thickness dimension for at least some tissue in-growth oriented in the longitudinal dimension. The oriented tissue in-growth coupled with cyclic straining and load sharing with the implant result in remodeling of new tissue in-growth to form oriented tendon-like tissue that strengthens the native tendon.

In some embodiments, the physical properties of the sheet-like structure result in load sharing between native tendon and the tendon repair implant immediately following surgery. In some embodiments, about 1% to about 50% of the load on the combination of native tendon and implant is carried by the implant. In some embodiments, about 5% to about 33% of the load is carried by the implant or sheet-like structure. Further, the sheet-like structure may be manufactured from a bioabsorbable or bioresorbable material so that over time the implant degrades and more of the load on the implant/native tendon combination is transferred to new tissue in-growth in the implant along with the native tendon.

The detailed disclosure also includes a method of treating a partial thickness tear in the supraspinatus tendon of the shoulder. The method includes providing a sheet-like structure having a first compact configuration for delivery from an arthroscopic instrument and a second planar configuration defined by a longitudinal, lateral and thickness dimension. The selected sheet-like structure may have a tensile modulus of about 1 MPa to about 100 MPa in the range of 1% to 3% strain in the longitudinal dimension and a porosity of about 30% to about 90% with longitudinal pathways defined in the longitudinal direction through the thickness dimension. In some embodiments, the tensile modulus is about 5 MPa to about 50 MPa in the range of 1% to 3% strain in the longitudinal direction. The shoulder may be arthroscopically accessed, in particular the bursal side surface of the supraspinatus tendon with the sheet-like structure in the first configuration. The sheet-like structure may then be deployed, transforming to the second planar configuration wherein a planar surface of the sheet-like structure extends over the partial thickness tear and is in contact with and generally conforms to the bursal surface of the tendon with the longitudinal dimension extending in the lengthwise direction of the tendon. The sheet-like structure may then be affixed to the tendon.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
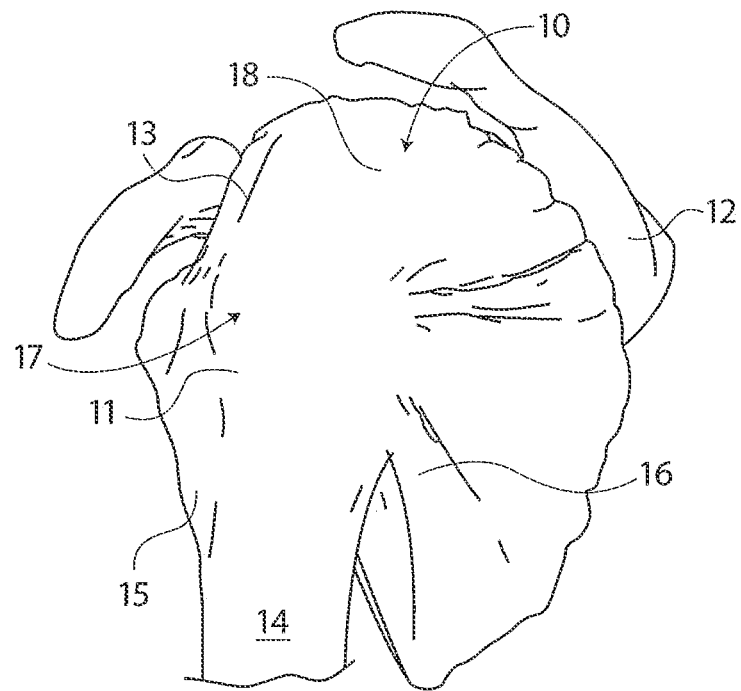
FIG. 1 is a simplified perspective view of the human rotator cuff and associated anatomical structure.
Figure 2:
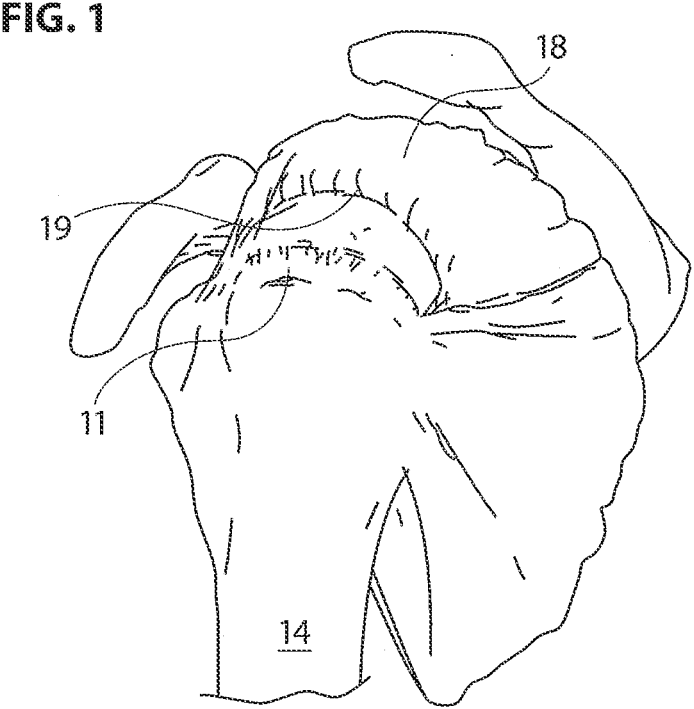
FIG. 2 is a schematic depiction of a full thickness tear in the supraspinatus tendon of the rotator cuff of FIG. 1.
Figure 3:
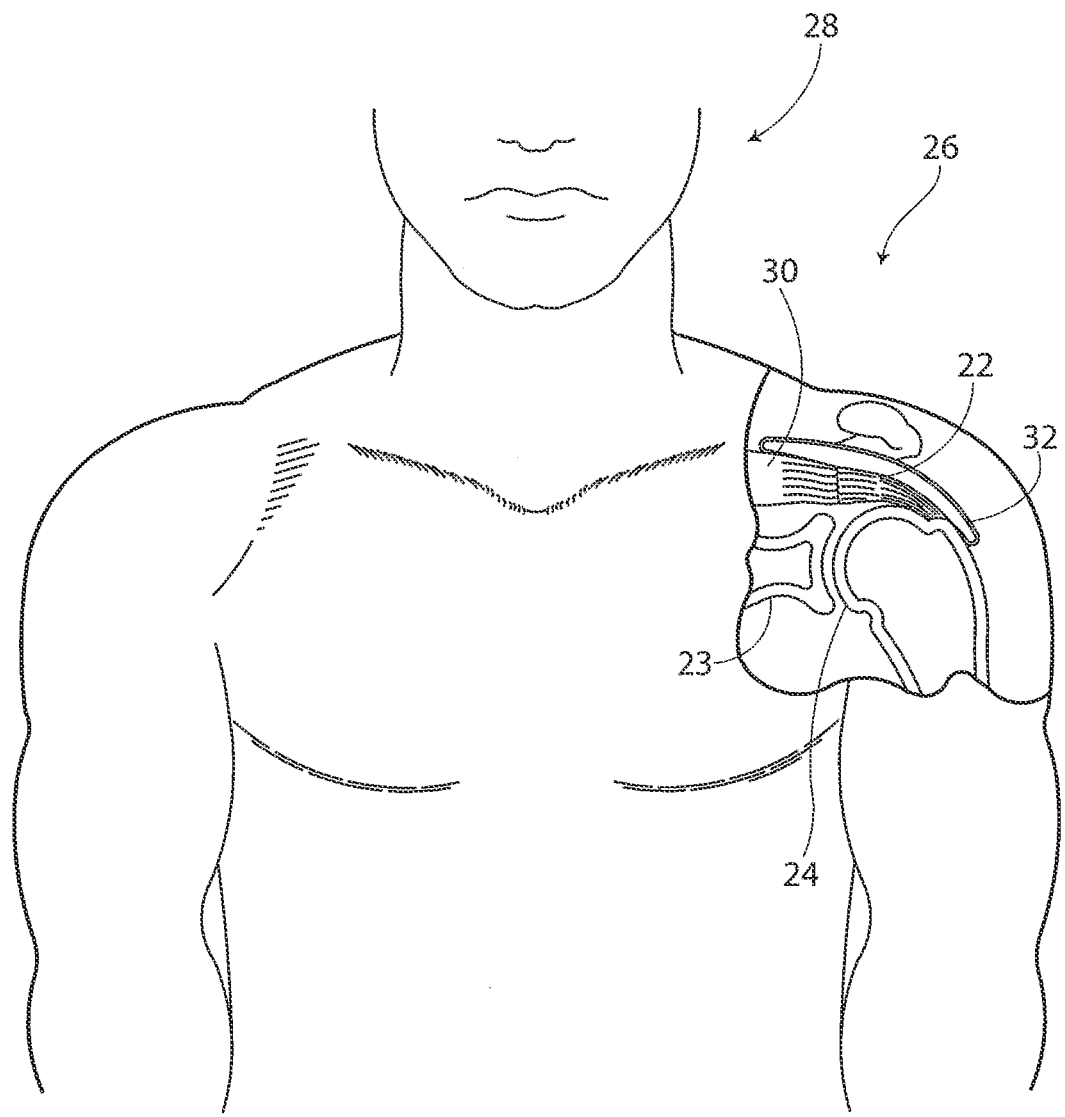
FIG. 3 is an anterior view showing the upper torso of a patient with the left shoulder shown in cross-section.

FIG. 3 is a stylized anterior view of a patient 28. For purposes of illustration, a shoulder 26 of patient 28 is shown in cross-section in FIG. 3. Shoulder 26 includes a humerus 24 and a scapula 23. The movement of humerus 24 relative to scapula 23 is controlled by the muscles of the rotator cuff as previously discussed with respect to FIG. 1. For purposes of illustration, only the supraspinatus 30 is shown in FIG. 3. With reference to FIG. 3, it will be appreciated that a distal tendon 22 of the supraspinatus 30 (hereinafter referred to as the supraspinatus tendon) meets humerus 24 at an insertion point 32.

Figure 4:
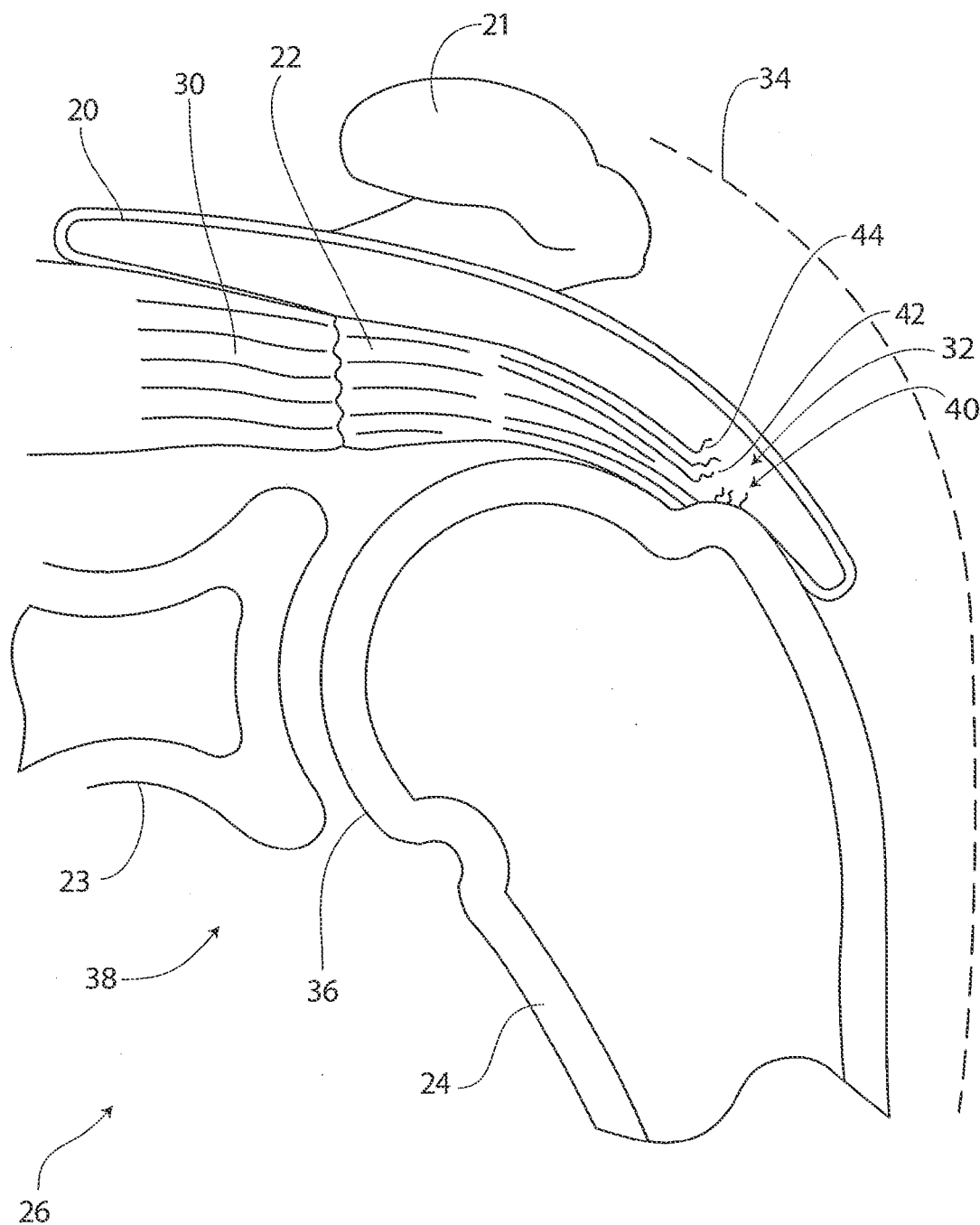
FIG. 4 is an enlarged, cross-sectional view showing the left shoulder depicted in FIG. 3.

FIG. 4 is an enlarged cross sectional view of shoulder 26 shown in the previous figure. In FIG. 4, a head 36 of humerus 24 is shown mating with a glenoid fossa of scapula 23 at a glenohumeral joint 38. The glenoid fossa comprises a shallow depression in scapula 23. A supraspinatus 30 and a deltoid 34 are also shown in FIG. 4. These muscles (along with others) control the movement of humerus 24 relative to scapula 23.

A distal tendon 22 of supraspinatus 30 meets humerus 24 at an insertion point 32. In the embodiment of FIG. 4, tendon 22 includes a damaged portion 140 located near insertion point 32. Damaged portion 40 includes a tear 42 extending partially through tendon 22. Tear 42 may be referred to as a partial thickness tear. The depicted partial thickness tear is on the bursal side of the tendon; however, the tear can be on the opposite or articular side of the tendon or may include internal tears to the tendon not visible on either surface. Tendon 22 of FIG. 4 has become frayed. A number of loose tendon fibers 44 are visible in FIG. 4.

Scapula 23 includes an acromium 21. In FIG. 4, a subacromial bursa 20 is shown extending between acromium 21 of scapula 23 and head 36 of humerus 24. In FIG. 4, subacromial bursa 20 is shown overlaying supraspinatus 30. Subacromial bursa 20 is one of more than 150 bursae found the human body. Each bursa comprises a fluid filled sac. The presence of these bursae in the body reduces friction between bodily tissues.

Figure 5:
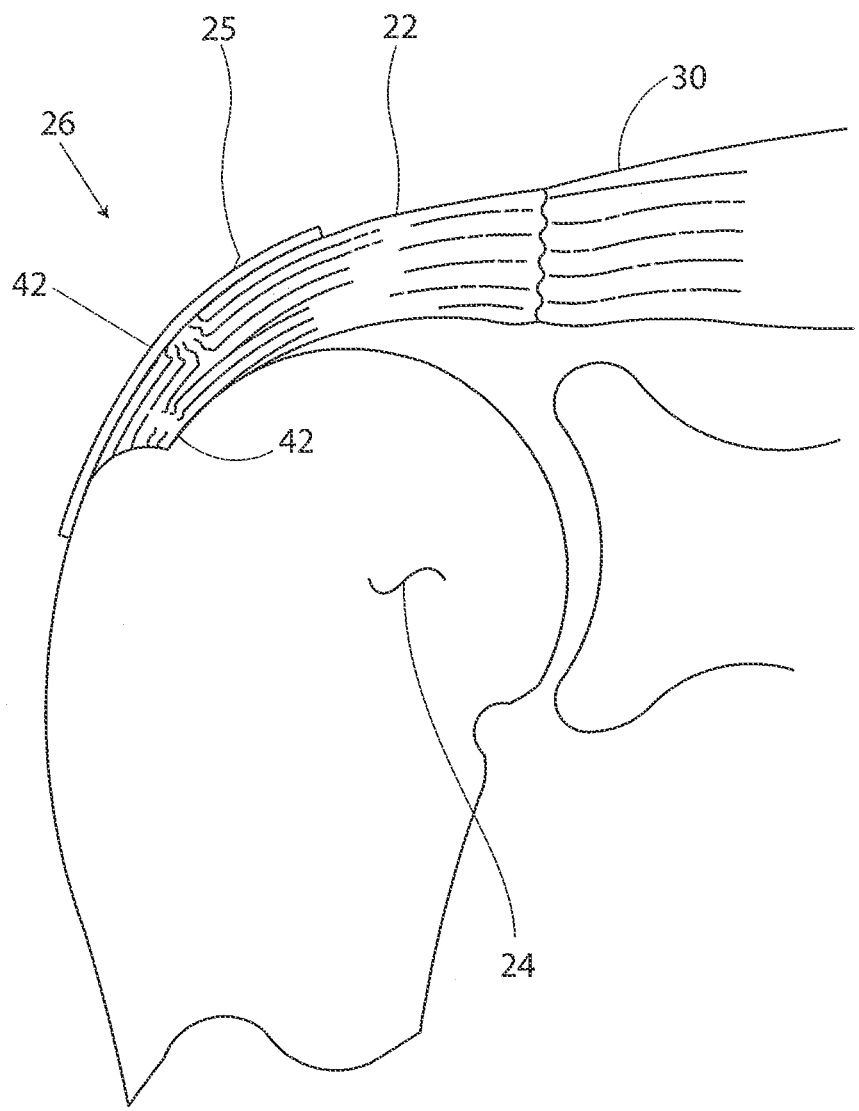
FIG. 5 is an enlarged schematic cross-sectional view of a shoulder showing partial thickness tears and an exemplary tendon repair implant positioned thereon.

FIG. 5 is an additional cross sectional view of shoulder 26 shown in the previous figure. In the embodiment of FIG. 5, a tendon repair implant 25 has been placed over the partial thickness tear 42. In this embodiment, the tendon repair implant 25 is placed on the bursal side of the tendon regardless of whether the tear is on the bursal side, articular side or within the tendon. Further, the tendon repair implant may overlay multiple tears, as also shown in FIG. 5.

In some embodiments, the tendon repair implant is engineered to provide a combination of structural features, properties and functions that are particularly appropriate for treating a partial thickness tear of less than 50% without physically cutting, then suturing the tendon, as is done in treating full thickness tears or partial thickness tears greater than 50%. These features may include: rapid deployment and fixation by arthroscopic means that compliment current procedures; tensile properties that result in desired sharing of anatomical load between the implant and native tendon during rehabilitation; selected porosity and longitudinal pathways for tissue in-growth; sufficient cyclic straining of the implant, having new tissue in-growth, in the longitudinal direction to promote remodeling of new tissue to tendon-like tissue; and, the tendon repair implant is bioresorbable or otherwise absorbable to provide transfer of additional load to native tendon over time.

In some embodiments, tendon repair implants are structured for rapid deployment and fixation by arthroscopic means to compliment current techniques used to relieve impingement or restricted movement of tendon relative to bone, such as acromioplasty and tunneling procedures in partial thickness tear treatments. The tendon repair implant 25 is a generally sheet-like structure that has a surface that conforms to the tendon surface when implanted. Further, the physical properties of the implant may be such that no significant pre-stretching or pre-loading of the implant during placement is required for it to function in sharing a sufficient portion of the anatomical load with the native tendon, as discussed below. Stated another way, the tensile properties of the implant may be designed to share a sufficient portion of the anatomical load present during rehabilitation by laying the implant in surface to surface contact with the tendon without any significant wrinkles Therefore, the tendon repair implant may be delivered in a folded, rolled or other reduced configuration through an arthroscopic instrument and spread out into the sheet-like shape with its surface in contact and generally conforming to the tendon surface without significant stretching before fixation to the tendon. Fixation may be accomplished via arthroscopic suturing or stapling techniques.

The sheet-like structure is defined by a longitudinal dimension, a lateral dimension and a thickness. In some embodiments, lateral and longitudinal dimensions of the implant may range from about 14 mm. to 24 mm. in the lateral direction and 20 mm. to 32 mm. in the longitudinal direction. The thickness of the sheet-like structure may be about 0.5 mm. to 2.5 mm. Upon implantation, the longitudinal dimension may extend generally in or parallel to the load bearing direction of the tendon. As depicted in the embodiment shown in FIG. 5, the longitudinal direction follows the supraspinatus tendon from its origin in the supraspinatus muscle down to the area of attachment on the humerus. As is well understood in the art, loading of the tendon is in this general direction upon contraction of the supraspinatus muscle.

Current procedures for repairing full thickness tears or partial thickness tears greater than 50% include cutting and suturing of the tendon itself and may include the addition of an implant that is designed to shield the tendon repair area from experiencing stresses during use. With current stress shielding implants the concern is the strain and load at which the implant versus the suture repair fails, as the goal is to prevent suture failure during excessive loading. In contrast, the tendon repair implants in some embodiments of the present disclosure have tensile properties to selectively share the anatomical load between damaged native tendon and the implant during the normal range of strains experienced during rehabilitation.

Figure 6:
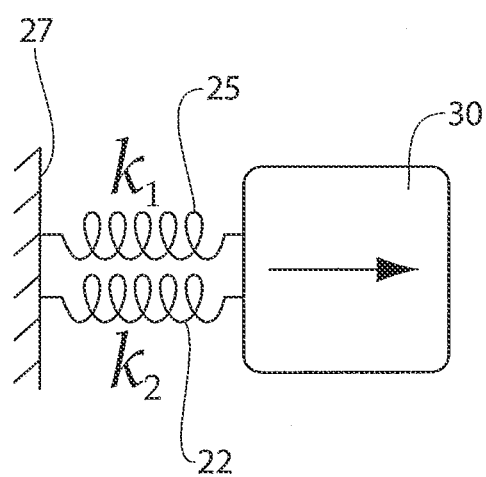
FIG. 6 is a schematic representation of the load sharing between the supraspinatus tendon and an exemplary tendon repair implant positioned and affixed thereon.

The tensile properties of some tendon repair implants described in the present disclosure for partial thickness tears less than 50% are engineered to selectively share the anatomical load during rehabilitation. The strain and loads experienced by the both the native tendon and affixed implant during use are explained with respect to the schematic diagram of FIG. 6. As installed over the damaged tendon, the tendon repair implant 25 and native tendon 22 are two generally parallel structures that each carry a portion of a load 27 generated by contraction of the supraspinatus muscle 30. The relative load carried by each depends on the tensile properties of the each structure. As parallel structures, the tendon repair implant 25 and the native tendon 22 each experience the same strain under a given load. It is known that native tendon will fail at strains of about 8%, and in normal use tendons experience less than 5% strain. In rehabilitation after surgery, the native tendon is exposed to strains of about 0% to 3%.

In some embodiments, tendon repair implants of the present disclosure are engineered with tensile properties in the range of 1% to 3% strain in order to properly share anatomical load during rehabilitation, as this is the range over which tensile properties affect the function of the implant. To accomplish load sharing, the tensile modulus of the implant should be less than the tensile modulus of the tendon which results in the load on the implant being less than the load on the native tendon. In some embodiments, the tensile modulus of the implant ranges from about 1 MPa. to about 100 MPa. In some embodiments, the tensile modulus is from about 20 to about 50 MPa. in the range of 1% to 3% strain. The value for a given material structure may be calculated from a best fit linear regression for data collected over the range of 1% to 3% strain. Depending upon the particular native tendon on which the implant is located, this may result in initial load sharing following surgery with about 1% to about 50% being carried by the implant. In some embodiments, about 10% to about 30% may be carried by the implant. The load on the supraspinatus tendon during rehabilitation may be about 50 N. to about 100 N., translating to a load on the implant of about 10 N to about 20 N. The tensile modulus can be measured with a 1 N. preload at zero strain and elongation rate of 1% per second after positioning the sheet-like structure in a generally flat and non-wrinkled format.

In some embodiments, a tendon repair implant of the present disclosure includes a selected porosity and longitudinal pathways for tissue in-growth. In some useful embodiments, the sheet-like structure of the implant comprises a material defining a plurality of pores that encourage tissue growth therein. The porosity and tissue in-growth allows for new collagen to integrate with collagen of the native tendon for functional load carrying. A coating that encourages tissue growth or in-growth may be applied to the surfaces of the sheet-like structure. It will be appreciated that sheet-like structure may comprise various pore defining structures without deviating from the spirit and scope of the present description. In some embodiments, the sheet-like structure has a pore size in the range of about 20 to about 400 microns. In some embodiments the pore size is in the range of about 100 microns to about 300 microns, and in some embodiments it is about 150 to about 200 microns. The porosity may be about 30% to about 90%, or it may be within the range of at least about 50% to about 80%. Examples of pore defining structures are discussed in more detail below for specific embodiments, but may include, but not be limited to open cell foam structures, mesh structures, micro-machined layered structures and structures comprising a plurality of fibers. In some embodiments, the fibers may be interlinked with one another. Various processes may be used to interlink the fibers with one another. Examples of processes that may be suitable in some applications include weaving, knitting, and braiding.

Tendon repair implants of the present invention may have a porosity greater than 50%, however, the porosity may be further structured to include tissue in-growth pathways in the longitudinal direction of the implant. Pathways may be included to extend through the thickness of the implant or laterally in the plane of the implant. Pathways may include segments extending longitudinally in the plane of the implant. In some embodiments, longitudinally extending pathways comprise a majority of the porosity with such pathway segments having cross sections of about 150 to about 200 microns. Longitudinal pathways may be open channels or lumens that extend in the longitudinal direction in the plane of the sheet-like structure when laying flat. They may be defined in the thickness of the sheet in the longitudinal direction. Further, these longitudinal pathways may generally be maintained when the implant is subjected to longitudinal loads experienced during rehabilitation.

A tendon repair implant may include tensile properties that allow for cyclic straining of the implant and new tissue in-growth to cause and facilitate remodeling of this new tissue to a more organized structure resembling tendon-like tissue. In some embodiments, the new tissue, based on the tensile properties of the implant, experiences tendon-like strain during rehabilitation. The tendon-like tissue, which may not be as strong as native tendon, has added load bearing strength in the longitudinal direction relative to unorganized tissue. This remodeling of tissue begins within 4 to 8 weeks after implant and continues for months. The strength of the new tissue continues to increase as collagen fibers become more oriented due to the proper strain signal resulting from the properties of the implant. To facilitate cyclic loading, the tendon repair implant may have a compressive modulus greater than the native tendon. A published value for the compressive modulus of the supraspinatus tendon is in the range of 0.02-0.09 MPa (J Biomech Eng 2001, 123:47-51). In some embodiments, the implant provided by the implantable device should have a higher compressive modulus than the tendon to prevent collapse of pores in the implant. The compressive modulus may be at least about 0.1 MPa, or at least about 0.2 MPa.

In some embodiments, the tendon repair implant is bioresorbable, biodegradable or otherwise absorbable to provide transfer of additional load to native tendon over time. By 2-3 months after implant, the new tissue in-growth should have gained strength through remodeling and it may be desirable to transfer more load from the implant to the new tissue and native tendon combination. Absorption of the implant enables the new tissue, in combination with the native tendon, to carry all of the load and develop optimal collagen fiber alignment. Further, absorption avoids potential long-term problems with particles from non-absorbable materials. The tissue within the device implant will typically be developing and organizing during the first one to three months after implantation, so load sharing with the implant is desired in some embodiments. After three months the tissue will typically be remodeling, so the mechanical properties of the implant should gradually decline to zero to enable the new tissue to be subjected to load without the implant bearing any of the load. If the implant loses modulus faster than it loses strength, then the relative loads on the implant will be less at three months than when first implanted. For example, if the modulus of the implant drops 50% to 25 MPa at three months, then 2% strain of the implant would require a stress of only about 0.5 MPa. At the same time, if the strength of the implant drops about 30% to 3.5 MPa, then the strength of the implant will be about seven times the anticipated loads at three months, compared to about five times when first implanted. Therefore, with the design criteria provided above, tensile failure of the implant during the first three months should be unlikely. Accordingly, the following specifications for degradation rate are recommended in some embodiments: an ultimate tensile strength of at least 70% strength retention at three months; tensile and compressive modulus of at least 50% strength retention at three months; and no minimum specification for strength and modulus at 6 months. The device may be designed to have a degradation profile such that it is at least 85% degraded in less than 1 to 2 years after implantation.

Cyclic creep is another design constraint to be considered in some embodiments. A strain of about 2% with a 30 mm long implant will result in an elongation of about only 0.6 mm. Therefore, very little cyclic creep can be tolerated in these embodiments to ensure that the implant will undergo strain with each load cycle. A test where a proposed implant design is cyclically strained to 2% at 0.5 Hz with rest periods for 8 hours provides 9000 cycles, which likely exceeds the number of cycles experienced in three months of rehabilitation of a patient's joint. Incorporation of relaxation times should be considered in such testing. In some embodiments, a maximum of about 0.5% creep is an acceptable specification.

In some useful embodiments, the tendon repair implant comprises one or more bioabsorbable materials. Examples of bioabsorbable materials that may be suitable in some applications include those in the following list, which is not exhaustive: polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly (amino acids), poly(alpha-hydroxy acid) or related copolymers materials.

The tendon repair implant may be configured to allow loading and retention of biologic growth factors. The implant and/or the growth factors may be configured to controllably release the growth factors. The implant may be configured to allow transmission of body fluid to remove any degradation bi-products in conjunction with a potential elution profile of biologics. The implant may also include platelet rich plasma at the time of implant or other biologic factor to promote healing and tissue formation.

A tendon repair implant of the present invention can include multiple layers or surface coatings. As implanted, the bursal side of the implant can include a layer or surface that will preferably slide against tissue without adherence. The tendon side of the implant may include a layer or coating that is more compatible with fixation to the tendon surface.

Various materials and formats may be used to produce tendon repair implants of the present invention. Each material and format is engineered to include selected material properties in the ranges discussed above. Material properties can be altered in the materials making up the sheet like structure or by altering the format or pattern of the material to adjust physical properties of the composite structure.

Figure 7:
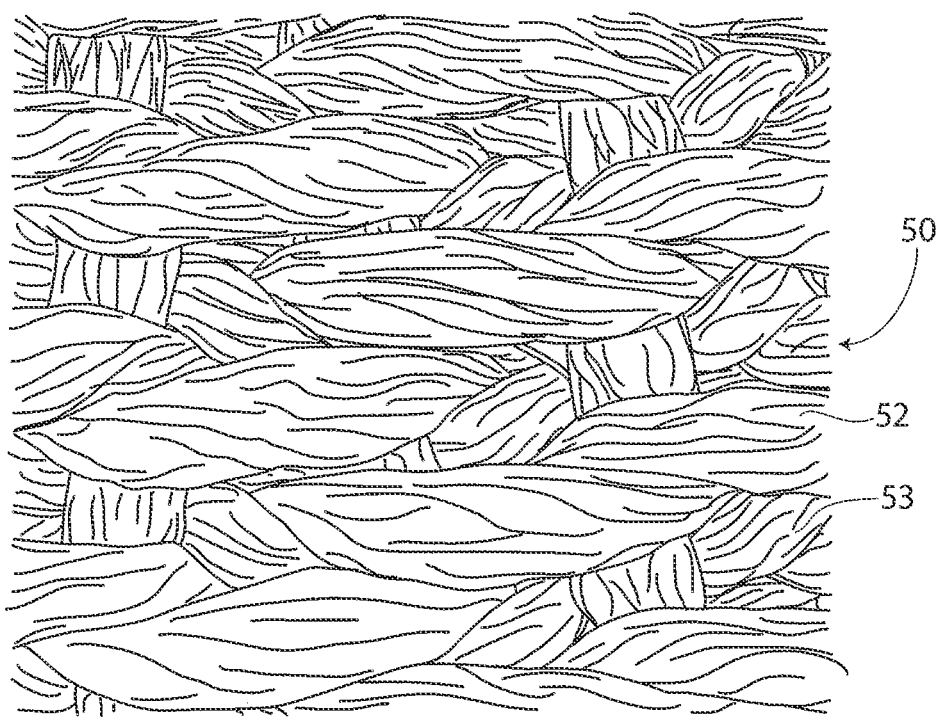
FIG. 7 is a magnified image of an exemplary tendon repair implant including a sheet-like structure having a woven strand and multifilament configuration.
Figure 8:
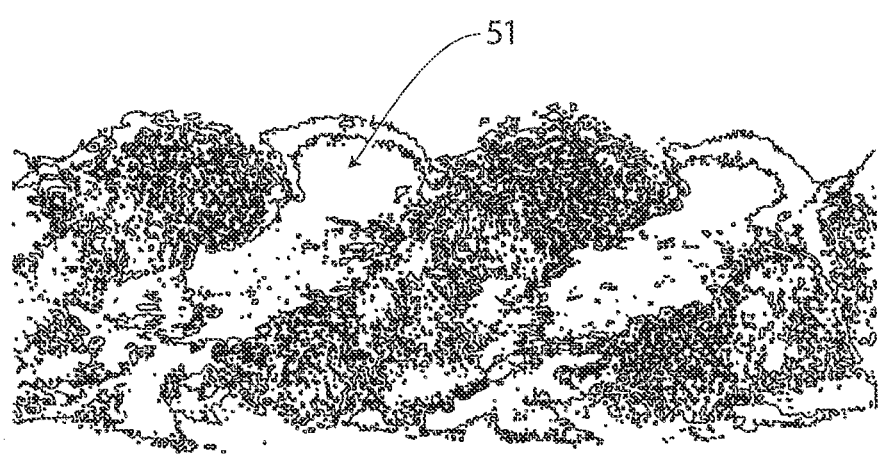
FIG. 8 is a magnified image of a cross section of the implant of FIG. 7.

One material and format for the sheet-like structure 50 is shown in FIG. 7. The structure 50 is a woven material including multiple strands 52 of a polymeric material, with each strand 52 including multiple filaments 53. The strands 52 include a weave pattern that forms longitudinally extending pathways 51 as depicted in the cross section view of FIG. 8. These longitudinally extending pathways have a cross section of about 150 to about 200 microns as indicated. One material for the filaments is poly-L-lactic acid.

Figure 9:
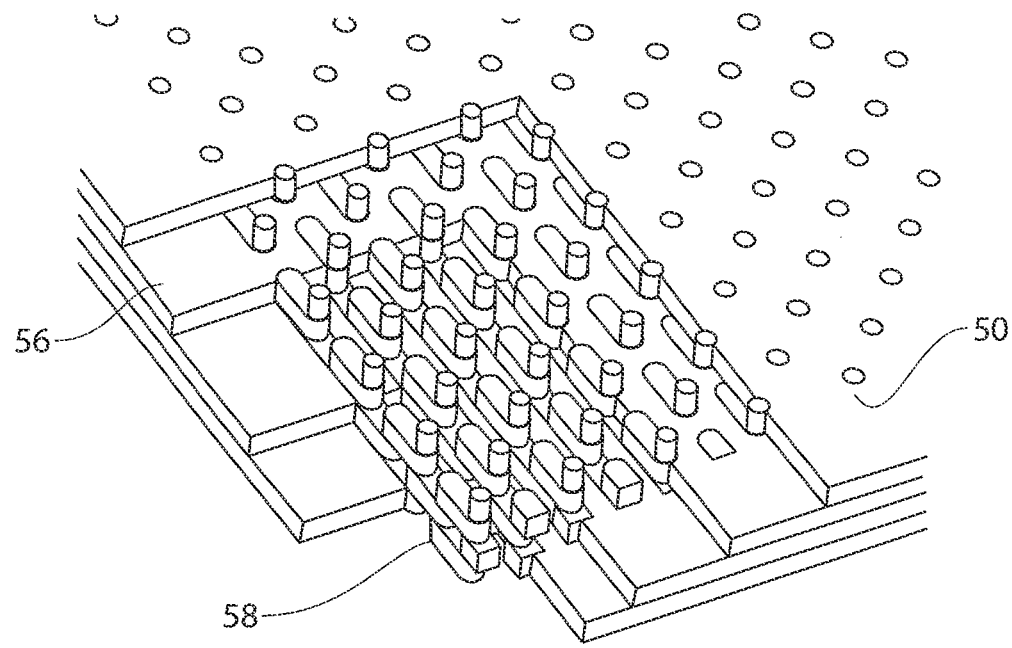
FIG. 9 is a representation of another exemplary tendon repair implant including a sheet-like structure having multiple layers of a micro-machined polymer material.
Figure 10:
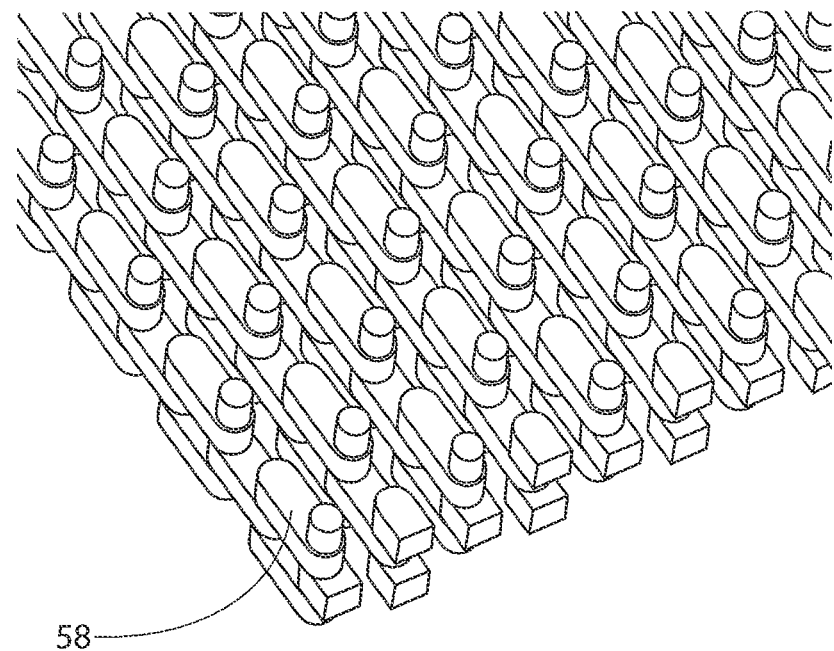
FIG. 10 schematically depicts the pattern of material removed from the structure of FIG. 9 illustrating the longitudinal pathways created through the structure.

An alternative material and format for the sheet-like structure 50 is shown in FIG. 9. The sheet-like structure 50 includes multiple layers 56 of micro-machined sheets. The composite of layered sheets form longitudinally extending pathways 58. This is best illustrated in FIG. 10, which shows the material that is removed from the sheets, indicating the pathways defined in the structure. These sheets are preferably made up of a blend of poly-L-lactic acid and polycaprolactone. Alternatively, individual sheets may be made of one or both of the polymers. The cross section of the longitudinally extending pathways may be about 150 to about 200 microns.

Figure 11:
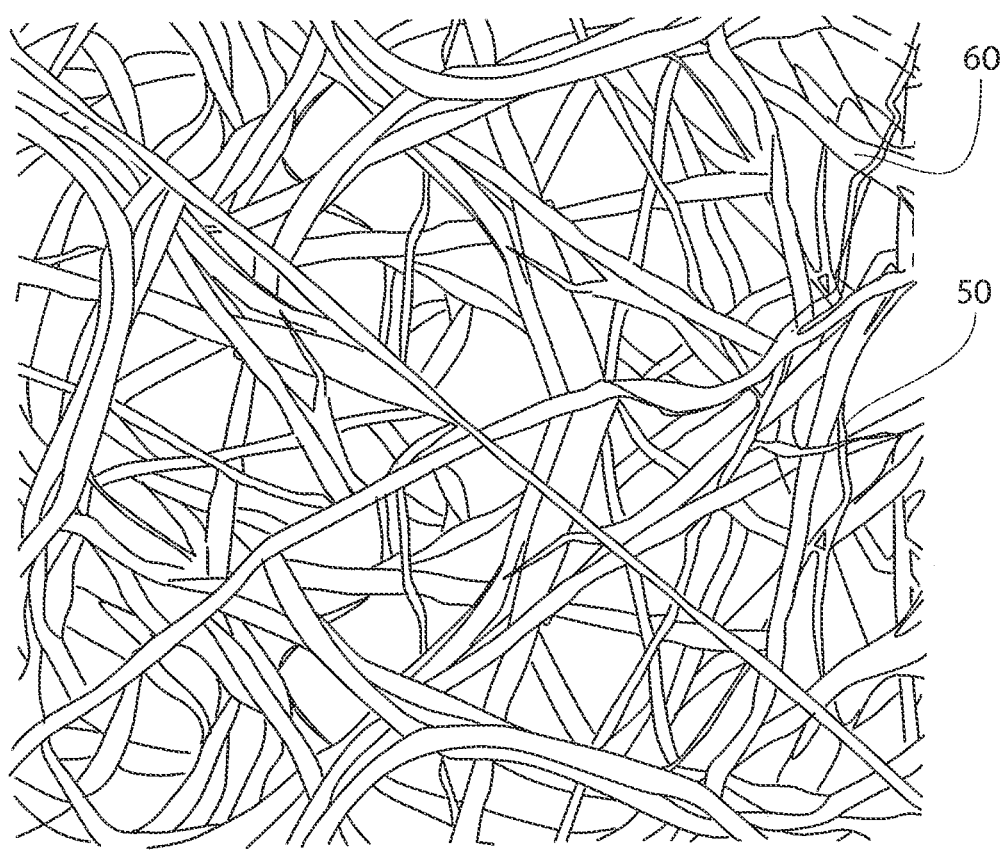
FIG. 11 is a magnified image of another exemplary tendon repair implant including a sheet-like structure having an array of nano-fibers forming the structure.

In another alternative material and format, the sheet-like structure 50 of the tendon repair implant is made up of electro-spun nano-fiber filaments 60 forming a composite sheet. An SEM of the composite structure is depicted in FIG. 11. The filaments have a cross section of about 5 microns. The filaments can be formed in a random pattern or can be aligned to alter the mechanical properties of the composite and create longitudinally extending pathways for tissue migration. The filaments may be made up of a blend of poly-L-lactic acid and polycaprolactone.

Figure 12:
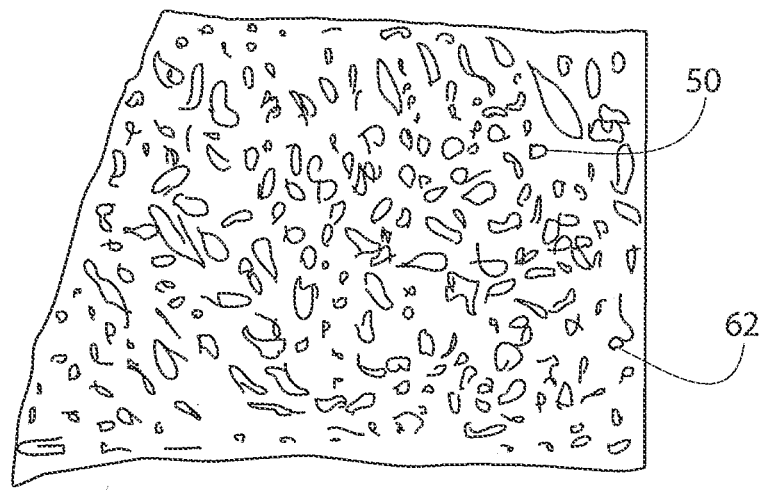
FIG. 12 is a magnified image of another exemplary tendon repair implant including a sheet-like structure formed from a synthetic sponge material.
Figure 13:
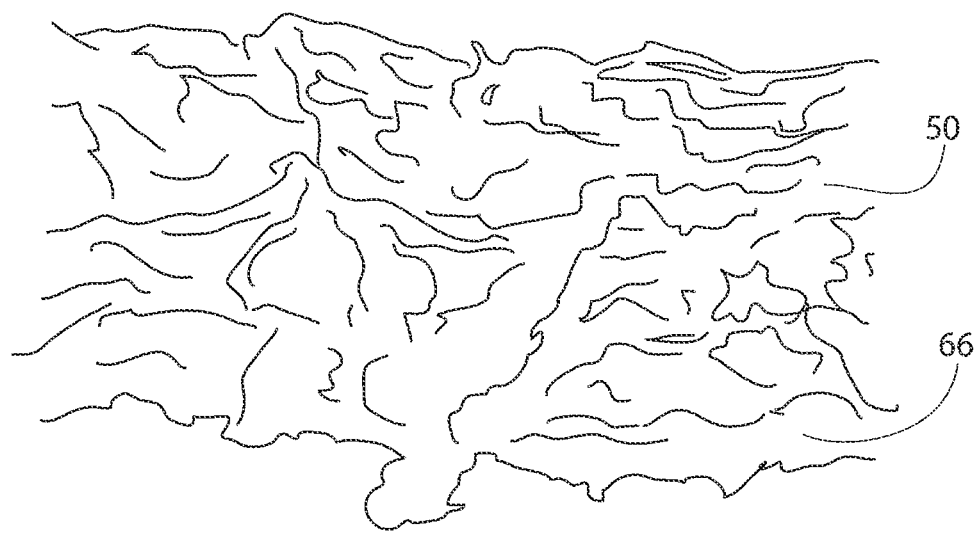
FIG. 13 is a magnified image of another exemplary tendon repair implant including a sheet-like structure formed from a reconstituted collagen material.

Another alternative material and format for the sheet-like structure 50 can include a synthetic sponge material as depicted in FIG. 12. As the SEM photograph indicates, longitudinally extending pathways are defined through the open cell structure. The open pores may be between about 150 to about 200 microns in cross section and may be interconnected in a random pattern. A similar cell structure can also be found in another alternative material and format manufactured from reconstituted collagen and depicted in the magnified image of FIG. 13. This structure includes longitudinal alignment of the collagen material to create longitudinal pathways 66. Physical properties of the collagen material may be adjusted through cross-linking. According to aspects of the present detailed disclosure, methods of treating a partial thickness tear in a tendon are also provided. In some methods, supraspinatus tendons having partial thickness tears of less than 50% are treated. The treatment site may be first arthroscopically accessed in the area of the damaged tendon. A tendon repair implant, such as previously described may be placed over a partial tear in a tendon. In some embodiments, the implant may be placed over a tendon having micro-tear(s), abrasions and/or inflammation. Left untreated, minor or partial tendon tears may progress into larger or full tears. According to aspects of the present disclosure, a small or partial tear may be treated by protecting it with a tendon repair implant as described above. Such early treatment can promote healing and prevent more extensive damage from occurring to the tendon, thereby averting the need for a more involved surgical procedure.

For arthroscopic delivery of the tendon repair implant, the implant may be configured to be collapsible so that it may be inserted into or mounted on a tubular member for arthroscopic insertion to the treatment site. For example, the implant and associated delivery device may be collapsed like an umbrella where the deployed delivery systems unfolds the pleats of the implant as mounted thereon to allow surface to surface engagement with the tendon without any substantial wrinkles Once flat against the tendon, the tendon repair implant may then be affixed using sutures or other suitable means such as staples such that the tensile properties will assure that the anatomical load will be shared because the native tendon and implant experience the same strain under load.

In summary, the tendon repair implant may comprise an absorbable material. In some embodiments, the purpose of the implant is to protect an injured portion of a tendon during healing, provide an implant for new tissue growth, and/or temporarily share some of the tendon loads. The implant may induce additional tendon-like tissue formation, thereby adding strength and reducing pain, micro strains and inflammation. When the implant is applied to a structurally intact, partially torn tendon, the initial loading of the implant may be less than that carried by native tendon tissue until collagen is formed during the healing process. In some embodiments, organized collagen fibers are created that remodel to tendon-like tissue or neo-tendon with cell vitality and vascularity. Initial stiffness of the device may be less than that of the native tendon so as to not overload the fixation while tendon tissue is being generated.

It is desirable in some situations to generate as much tissue as possible within anatomical constraints. In some cases where a tendon is degenerated or partially torn, tendon loads are relatively low during early weeks of rehabilitation. For example, the load may be about 100 N. The strain in the tendon due to the load during rehabilitation can be about 2%. In some of these cases, the tendon repair implant can be designed to have an ultimate tensile strength of at least about 2 MPa. The tensile modulus may be designed to be no more than about 50 MPa and no less than about 5 MPa. The compressive modulus may be designed to be at least about 0.2 MPa. With a tensile modulus of 5 MPa, in order for the implant to strain 2% in conjunction with the degenerated tendon, the stress on the implant will be about 1.0 MPa. With an ultimate tensile strength of 2 MPa, the strength of the sheet-like structure of the implant when first implanted will be about two times the expected loads. With a cross-sectional area of 20 mm2, the load on the implant will be 20 N. Thus, from a load sharing perspective, the implant will carry about 20% of the load to experience 2% strain.

Material(s) used in the implanted device should be able to withstand the compression and shear loads consistent with accepted post-surgical shoulder motions. The perimeter of the device may have different mechanical properties than the interior of the device, such as for facilitating better retention of sutures, staples or other fastening mechanisms. The material(s) may be chosen to be compatible with visual, radiographic, magnetic, ultrasonic, or other common imaging techniques. The material(s) may be capable of absorbing and retaining growth factors with the possibility of hydrophilic coatings to promote retention of additives.

While exemplary embodiments of the present invention have been shown and described, modifications may be made, and it is therefore intended in the appended claims to cover all such changes and modifications which fall within the true spirit and scope of the invention.

What is claimed is:

1. A tendon repair implant for repair of a partial thickness tear of a tendon, the tendon repair implant comprising:
    a sheet-like structure formed of reconstituted collagen material, the sheet-like structure defined by a longitudinal dimension aligned with a load bearing direction of the tendon when positioned thereon, a lateral dimension, and a thickness dimension, wherein the longitudinal dimension is greater than the lateral dimension and the thickness dimension, the sheet-like structure having an initial tensile modulus in the longitudinal dimension of 1 MPa to 50 MPa in the range of 1% to 3% strain prior to implantation, where 0% strain is defined with a 1 N preload applied to the sheet-like structure, and a porosity of 30% to 90% for tissue in-growth,
    wherein the reconstituted collagen material has a longitudinal alignment of collagen fibers forming longitudinal pathways extending along the longitudinal dimension of the sheet-like structure, and
    wherein the sheet-like structure is adapted to conform to the surface of the tendon and is configured to have an initial load share representing between 1% to 50% of an anatomical load applied to the tendon and sheet-like structure at the time that the sheet-like structure is affixed to the tendon.

2. The tendon repair implant of claim 1, wherein the initial load share comprises between 0.5 N and 50 N.

3. The tendon repair implant of claim 1, wherein the initial load share comprises between 0.5 N and 25 N.

4. The tendon repair implant of claim 1, wherein the initial tensile modulus is 5 MPa to 20 MPa.

5. The tendon repair implant of claim 1, wherein the sheet-like structure is configured to degrade in tensile strength from an initial tensile strength thereby sharing less of the anatomical load over time.

6. The tendon repair implant of claim 5, wherein the sheet-like structure is configured to retain at least 70% of the initial tensile strength three months after being affixed to the tendon and to retain at least 50% of the initial tensile modulus and 50% of an initial compressive modulus three months after being affixed to the tendon.

7. The tendon repair implant of claim 1, wherein the sheet-like structure is bioresorbable.

8. The tendon repair implant of claim 1, wherein the sheet-like structure is further configured to be attached to the surface of the tendon without pre-loading or pre-stretching.

9. The tendon repair implant of claim 1, wherein the sheet-like structure has one or more agents affixed thereto which promote tissue in-growth.

10. The tendon repair implant of claim 1, wherein the sheet-like structure includes pores having sizes between 20 microns and 400 microns.

11. The tendon repair implant of claim 1, wherein the longitudinal dimension is in the range of 20 mm to 32 mm, the lateral dimension is in the range of 14 mm to 24 mm, and the thickness dimension is in the range of 0.5 mm to 2.5 mm.

12. The tendon repair implant of claim 1, wherein the sheet-like structure has a maximum of 0.5% creep over three months.

13. The tendon repair implant of claim 1, wherein the sheet-like structure has a compressive modulus greater than the tendon to allow for cyclic straining of the sheet-like structure and any tissue in-growth.

14. The tendon repair implant of claim 13, wherein the longitudinal pathways comprise lumens.

15. The tendon repair implant of claim 13, wherein the longitudinal pathways are maintained when the sheet-like structure is subjected to longitudinal loads.

16. The tendon repair implant of claim 13, wherein the sheet-like structure has a porosity of at least 50% to 80%.

17. The tendon repair implant of claim 13, wherein the compressive modulus is at least 0.1 MPa.

18. The tendon repair implant of claim 1, wherein the longitudinal pathways have a cross section of 150 microns to 200 microns.

19. A tendon repair implant for repair of a partial thickness tear of a tendon, the tendon repair implant comprising:
  a sheet-like structure formed of reconstituted collagen material, the sheet-like structure defined by a longitudinal dimension aligned with a load bearing direction of the tendon when positioned thereon, a lateral dimension, and a thickness dimension, wherein the longitudinal dimension is greater than the lateral dimension and the thickness dimension, the sheet-like structure having an initial tensile modulus in the longitudinal dimension of 1 MPa to 50 MPa in the range of 1% to 3% strain prior to implantation, where 0% strain is defined with a 1 N preload applied to the sheet-like structure, wherein the sheet-like structure is flexible such that when the sheet-like structure is affixed to a surface of the tendon the sheet-like structure conforms to the surface of the tendon;
  wherein the reconstituted collagen material has a longitudinal alignment of collagen fibers forming longitudinal pathways extending along the longitudinal dimension of the sheet-like structure, wherein the longitudinal pathways have a cross section of 150 microns to 200 microns for at least some tissue in-growth oriented in the longitudinal dimension;
  the sheet-like structure being configured to initially have an initial load share representing between 1% and 50% of a load applied to the tendon; and
  the sheet-like structure being configured to degrade in tensile strength from an initial tensile strength thereby sharing less of the load applied to the tendon over time.

20. The tendon repair implant of claim 19, wherein the sheet-like structure is configured to initially share between 5% and 33% of the load of the tendon.

21. The tendon repair implant of claim 19, wherein the initial load share comprises between 0.5 N and 50 N.

22. The tendon repair implant of claim 19, wherein the initial load share comprises between 0.5 N and 25 N.

23. The tendon repair implant of claim 19, wherein the initial tensile modulus is 20 MPa to 50 MPa.

24. The tendon repair implant of claim 19, wherein the sheet-like structure is configured to retain at least 70% of the initial tensile strength three months after being affixed to the tendon and to retain at least 50% of the initial tensile modulus and at least 50% of an initial compressive modulus three months after being affixed to the tendon.

25. The tendon repair implant of claim 19, wherein the sheet-like structure is bioresorbable.

26. The tendon repair implant of claim 19, wherein the sheet-like structure is further configured to be attached to the surface of the tendon without pre-loading or pre-stretching.

27. The tendon repair implant of claim 19, wherein the sheet-like structure has one or more agents affixed thereto which encourage tissue in-growth.

28. The tendon repair implant of claim 19, wherein the longitudinal dimension is in the range of 20 mm to 32 mm, the lateral dimension is in the range of 14 mm to 24 mm, and the thickness dimension is in the range of 0.5 mm to 2.5 mm.

29. The tendon repair implant of claim 19, wherein the sheet-like structure has a porosity of 30% to 90%.

30. A tendon repair implant for repair of a partial thickness tear of a supraspinatus tendon having a load bearing direction, the tendon repair implant comprising:
  a sheet-like structure formed of reconstituted collagen material, the sheet-like structure having a longitudinal dimension, a lateral dimension, and a thickness dimension and configured to be affixed to a surface of the supraspinatus tendon such that the longitudinal dimension of the sheet-like structure extends parallel to the load bearing direction of the supraspinatus tendon;
  wherein the sheet-like structure has an initial tensile modulus in the longitudinal dimension of 5 MPa to 50 MPa in the range of 1% to 3% strain prior to implantation, where 0% strain is defined with a 1 N preload applied to the sheet-like structure;
  wherein the reconstituted collagen material has a longitudinal alignment of collagen fibers forming a plurality of longitudinal pathways that encourage tissue in-growth therein, wherein the longitudinal pathways extend along the longitudinal dimension of the sheet-like structure and have cross sections of 150 microns to 200 microns; and
  wherein the sheet-like structure has a compressive modulus greater than the supraspinatus tendon to allow for cyclic straining of the sheet-like structure and any tissue in-growth, wherein the compressive modulus is at least 0.1 MPa; and
  wherein when affixed to the surface of the supraspinatus tendon, the sheet-like structure is configured to initially share between 1% and 50% of a load applied to the supraspinatus tendon.

31. The tendon repair implant of claim 30, wherein between 1% and 50% of the load applied to the supraspinatus tendon comprises between 0.5 N and 50 N.

32. The tendon repair implant of claim 30, wherein between 1% and 50% of the load applied to the supraspinatus tendon comprises between 0.5 N and 25 N.

* * * * *